United States Patent [19]

Kovacs

[11] 4,445,894
[45] May 1, 1984

[54] BAND FOR ANCHORING A CATHETER OR OTHER DEVICE TO THE BODY

[75] Inventor: Joseph Kovacs, Cranston, R.I.

[73] Assignee: Baka Manufacturing Company, Inc., Plainville, Mass.

[21] Appl. No.: 407,456

[22] Filed: Aug. 12, 1982

[51] Int. Cl.³ .......................................... A61M 25/02
[52] U.S. Cl. ........................... 604/179; 128/DIG. 26
[58] Field of Search ...................... 604/179, 174, 0.33; 128/DIG. 15, DIG. 26

[56] References Cited

U.S. PATENT DOCUMENTS

| | | | |
|---|---|---|---|
| 3,726,280 | 4/1973 | Lacount | 604/179 |
| 3,765,421 | 10/1973 | Poppik | 128/DIG. 26 |
| 3,878,849 | 9/1975 | Muller et al. | 604/179 |
| 4,096,863 | 6/1978 | Kaplan | 128/DIG. 26 X |

Primary Examiner—Stephen C. Pellegrino
Attorney, Agent, or Firm—Wolf, Greenfield & Sacks

[57] ABSTRACT

A band for securing a catheter or similar device to a limb of a human comprising a stretchable primary strap adapted to encircle a limb. A part of the strap is made of a soft looped fabric and the strap also carries a male Velcro-type fastening material which cooperates with the looped fabric to enable the strap to be secured in place about the limb. A secondary strap made of a flexible material is secured, hooks up, intermediate its ends to the central portion of the primary strap on the looped fabric. The secondary strap is made of a male Velcro-type fastening material, and each end of the secondary strap is designed to be looped over and encircle the catheter or similar device and attach to the looped fabric to hold the catheter or similar device securely in place on the limb.

7 Claims, 7 Drawing Figures

BAND FOR ANCHORING A CATHETER OR OTHER DEVICE TO THE BODY

INTRODUCTION AND BACKGROUND

This invention relates to a new and improved band for securing catheters and similar devices to the limb of a human. More particularly, this invention comprises an improvement over the devices shown in U.S. Pat. Nos. 3,765,421 and 3,878,849 and provides certain advantages over the device shown in U.S. Pat. No. 4,096,863 assigned to the assignee of this application.

There are presently a number of devices on the market for securing catheters and similar devices to a limb. These devices perform a very useful function. They are both a convenience to the attendant applying the device to the patient and a comfort to the patient. The present invention is intended to improve the performance of such devices.

One important object of this invention is to provide a band of the class described which is infinitely adjustable in size both with respect to the size of the limb to which it is to be attached and to the size of the device which it is to support.

Another important object of this invention is to provide a band of the class described which is very simple to manufacture and easy to apply.

Still another object of this invention is to provide a band of the class described, which is comfortable when worn and remains in place on the limb until intentionally removed.

Yet another important object of this invention is to provide a catheter band that enables the attending doctor or nurse to apply catheter traction to the device that discourages self removal of the drain tube.

To accomplish these and other objects, the band of this invention includes a primary strap made of a stretchable section and a non-stretchable section attached end to end and adapted to encircle the limb to which it is to be attached. The non-stretchable section carries a looped material on its outer surface which together with a male Velcro-type fastening material at the free end of the stretchable section provides means for closing the strap about the limb. A secondary strap made of a male Velcro-type fastening material is secured intermediate its ends, hooks up, to the upper side of the non-stretchable part of primary strap on the looped material, and the ends of the secondary intermediate are intended to be turned over and extend in opposite directions to form a pair of loops that encircle the catheter or other device to be anchored to the limb. The Velcro-like material of the secondary strap cooperates with the looped material forming part of the primary strap for locking the ends of secondary strap closed about the device.

In prior U.S. Pat. No. 4,096,863, the secondary strap is threaded through an eyelet connected to one end thereof to form a loop about the catheter. While the configuration performs very well and has met with substantial commercial success, the configurations of the present invention are somewhat easier to use and less expensive to manufacture. The prior devices shown in U.S. Pat. Nos. 3,765,421 and 3,878,849 do not hold the catheter or other device firmly in place and are not capable of holding a wide variety of tube sizes as they are not adjustable over a wide range of sizes.

In each of the embodiments of the present invention, the ends of the secondary strap are designed to pull the tubular device in opposite directions so as to form a firm grip on the device. The loops formed by the ends of the secondary strap are infinitely adjustable so that a very wide variety of tube sizes may be accommodated.

These and other objects and features of this invention will be better understood and appreciated from the following detailed description of two embodiments thereof, selected for purposes of illustration and shown in the accompanying drawing.

BRIEF FIGURE DESCRIPTION

DETAILED DESCRIPTION

The band shown in FIGS. 1–4 is illustrated as it may support a catheter tube T to the thigh of a patient's leg. The band includes a primary strap 10 and a secondary strap 12.

Figure 1:
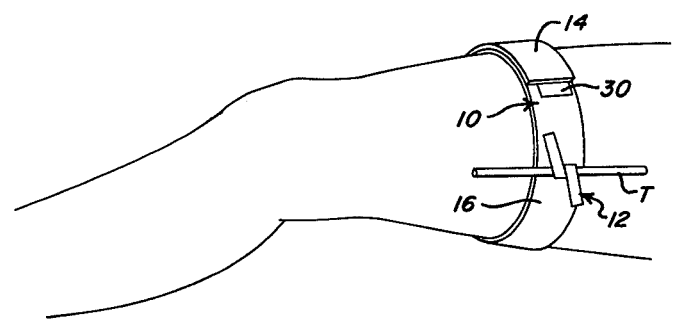
FIG. 1 is a fragmentary perspective view of a leg of a human, to which one embodiment of this invention is secured and suggesting the manner in which the band retains a catheter along the leg.
Figure 2:
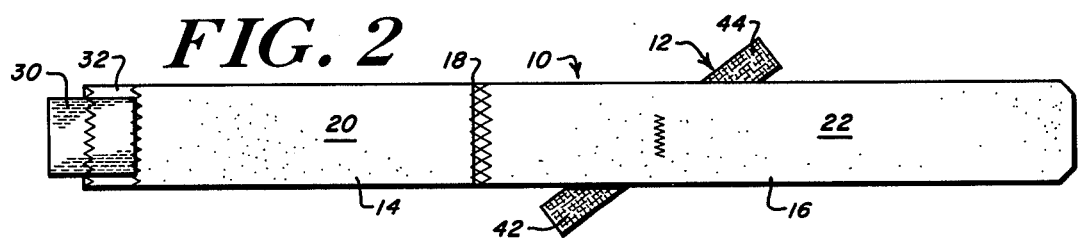
FIG. 2 is a plan view of the inner surface of the band shown in FIG. 1.
Figure 3:
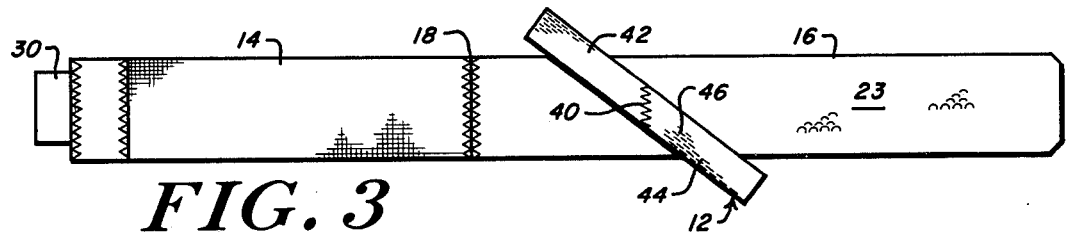
FIG. 3 is a plan view of the outer surface of the band shown in FIG. 1.
Figure 4:
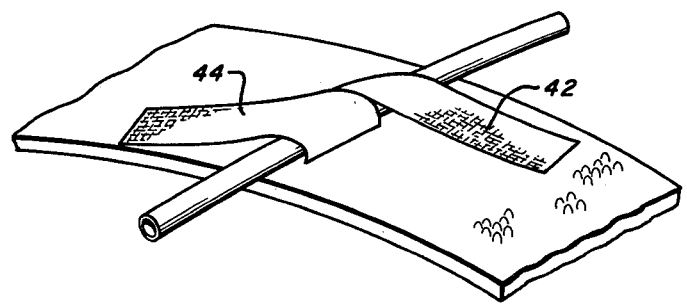
FIG. 4 is an enlarged fragmentary perspective view of the band of FIG. 1 and showing how the secondary band holds the catheter or similar device in locked position.

The primary strap 10 is made in two sections 14 and 16 sewn end to end as suggested at 18 in FIGS. 2 and 3. Section 14 is made of an elastic webbing material which is stretchable in a lengthwise direction but is of a relatively fixed dimension across its width. The inside surface of the webbing carries a soft lining material suggested at 20 which may be in the form of a Helenca backing or some other soft material which is comfortable to the skin but which does not interfere with the elasticity of webbing 14. The non-stretchable section 16 is made of an inexpensive laminate having a very light, soft foam core with a soft cotton lining 22 on the inside and looped cotton fabric 23 on the outside.

Typically, section 14 may be nine inches in length and section 16 about fourteen inches in length, and the band is of uniform width, approximately two inches wide.

A small patch of male Velcro-type fastening material 30 is stitched to the inner or lining side 20 of section 14 at its free end 32 with the hook-like barbs of the Velcro-type material facing away from the lining. When the primary strap 10 is wound about the limb, the lined surfaces 20 and 22 shown in FIG. 2 are placed against the skin, and the strap encircles the limb with the end 32 of the strap overlapping section 16. When applied in that fashion, the Velcro-type strip 30 faces the upper looped fabric 23 of section 16, and the barbs engage the loops to releasably lock the ends together with the strap fairly tightly encircling the limb. This is clearly shown in FIG. 1. Because section 14 is stretchable, the attendant can apply the strap 10 with sufficient tension so that the limb is firmly gripped by the band and held in place but without applying so much pressure to the limb as to cut off circulation. Further, because the Velcro-type patch 30 may be attached to any portion of section 16, the diameter of the encircling band is infinitely adjustable between the maximum expanded length of the strap and the relaxed length of section 14, and the patch 30 may overlap the major portion of section 16 up to the location of secondary strap 12.

While primary strap 10 is bound about the limb of the patient, secondary strap 12 made of a male Velcro-type fastening material is used to anchor the tube T in place. In the embodiment of FIGS. 1–4 the strap 12 is made of a single length of Velcro-type material approximately six inches in length and ⅜ inch wide and is sewn at its center to the looped material 23 on the front or upper face of the primary strap section 16 at an angle of approximately 30° to the primary strap, and the hooks of the secondary face away from the looped material. In FIGS. 2 and 3 the stitching is suggested at 40. The two halves 42 and 44 of the strap 12 on opposite sides of the stitching 40 are each adapted to be looped over the tubular member T to be held by the strap and be held in that position by engagement of the hooks of the Velcro-type material with the looped fabric 23 on the upper surface of section 16 of the primary strap 10. When the halves of the secondary strap 12 are looped over the tube T, the hooks on surface 46 face the looped fabric so that the two may readily engage one another. The angular disposition of the secondary strap allows each half 42 and 44 to loop over the tube T without interference with one another as is clearly shown in FIG. 4, and each half bears against the tube to provide very considerable area of frictional contact between the secondary strap and tube. Furthermore, the strap halves may be pulled tightly over the tube in opposite directions to maximize the frictional contact with the tube and thereby hold it firmly in place.

Figure 5:
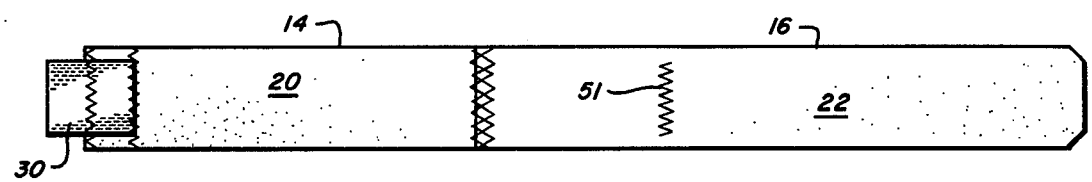
FIGS. 5, 6 and 7 are views similar to FIGS. 2, 3 and 4 and showing a second embodiment of this invention.
Figure 6:
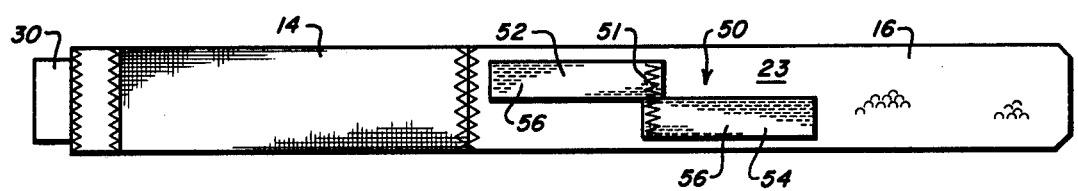
Figure 7:
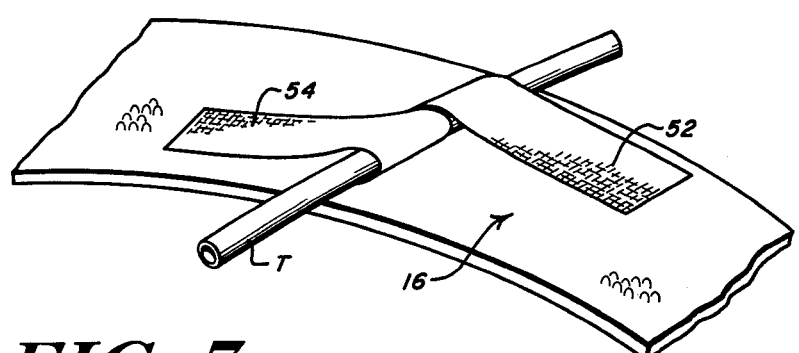

The embodiment of FIGS. 5–7 differs from that of FIGS. 1–4 only in the configuration of the secondary strap. The rest of this embodiment is identical to the first, and like parts bear the same reference characters.

In FIGS. 5–7, the secondary strap 50 is shown to be made up of two shorter lengths 52 and 54 of Velcro-type fabric each secured at one end to the looped fabric on the front face of section 16 of primary strap 10 by stitching 51. Each length 52 and 54 effectively is half the secondary strap, and each is approximately 6 inches long and ⅜ inch wide. The two halves are parallel to but offset from one another and each is parallel to the primary strap. The hooked surfaces 56 of halves 52 and 54 face upwardly away from the looped surface 23, and each half can be looped over the tube T in the same fashion as the halves 42 and 44 of the secondary strap of the first embodiment. As the halves are offset, each can extend over the tube T without interference with the other, and each half engages the tube over an area whose width is the full width of the strap to maximize the frictional contact between the secondary strap and the tube.

From the foregoing description of the two embodiments of this invention, it will be apparent that the band may readily be applied to the patient and will continue to function effectively so long as it is not intentionally disturbed. Unlike the prior art devices known to applicant, the tube T supported by the secondary strap will not readily loosen because the size of the loop encircling the tube is fixed by the locked Velcro-type fasteners of the secondary strap. The substantial length of locking engagement between the secondary strap and looped fabric 23 ensures foam support for the tube. To enlarge the size of the loop encircling tube T, the halves 42 and 44 or 52 and 54 must be lifted from the looped material 23 and only after the locking action of the barbs and loops is completely interrupted can the strap 12 release tube T. It will also be appreciated that the attendant need not thread the secondary strap through an eyelet but rather must perform only the simplest operation of merely pulling the ends of the secondary strap over the tube T and pressing the halves against the looped surface. This may be done any place on the tube or even at the crotch of the tube as selected by the attendant. And the secondary strap is of minimum cost. The separate halves of the secondary strap enables it to engage separage portions of the tubular member or two diverging arms of a catheter.

From the foregoing description, those skilled in the art will appreciate that modifications may be made of this invention without departing from its spirit. Therefore, I do not intend to limit the scope of this invention to the two embodiments illustrated and described. Rather, it is intended that the scope of this invention be determined by the appended claims and their equivalents.

What is claimed is:

1. A band for anchoring a catheter or other tubular device to the body comprising an extendable primary strap adapted to encircle the portion of the body to which the device is to be anchored and having upper and inner surfaces, said upper surface including a length of material to which the hooks of Velcro-like material can operatively attach and said inner surface intended to lie against the body,
   fastening means connected to the primary strap for securing it in place on the body,
   a secondary strap made of a Velcro-type material and connected intermediate its ends to the central portion of the upper surface of the primary strap with the hooks of the Velcro-type material facing upwardly from the upper surface of the primary strap,
   each end of the secondary strap being adapted to be looped over the tube in opposite directions and with the hooks of the Velcro-type material operatively attaching to the hook attaching material of the primary strap to hold the tubular device.

2. A band for anchoring a catheter or other tubular device to the body comprising
   an extendable primary strap adapted to encircle the portion of the body to which the device is to be anchored and having upper and inner surfaces, said upper surface including a length of soft looped material and said inner surface intended to lie against the body,
   fastening means connected to the primary strap for securing it in place on the body,
   a secondary strap made of Velcro-type material and connected intermediate its ends to the soft looped material of the primary strap at the central portion of the upper surface of the primary strap with the hooks of the Velcro-type material facing upwardly from the upper surface of the primary strap,
   each end of the secondary strap being adapted to be looped over the tube in opposite directions with the hooks of the Velcro-type material operatively attaching to the soft looped material of the primary strap to hold the tubular device.

3. A band as described in claim 2 further characterized by
   said primary strap also including a section of male Velcro-type fastening material forming part of the first recited fastening means together with the looped material.

4. A band as described in claim 1 further characterized by
said secondary strap being secured at its mid point to the primary strap and being disposed at an angle to the primary strap.

5. A band as described in claim 1 further characterized by
said secondary strap being made of two lengths of Velcro-type material, each length being generally parallel to and offset from the other and being generally parallel to the primary strap.

6. A band as described in claim 3 further characterized by
said secondary strap being made of two parts offset from one another so that each end of the strap can be looped over the tube without overlapping the other end.

7. A band as described in claim 3 further characterized by
said secondary strap being disposed at an angle to the main strap permitting each end of the strap to be looped over the tube without overlapping the other end of the tube.

* * * * *